United States Patent
Hagen et al.

(10) Patent No.: US 6,348,043 B1
(45) Date of Patent: Feb. 19, 2002

(54) MULTI-DOSE INFUSION PUMP PROVIDING MINIMAL FLOW BETWEEN DOSES

(75) Inventors: Jeffrey A. Hagen, Longmont; David W. Skinkle, Denver, both of CO (US)

(73) Assignee: McKinley Medical, LLLP, Wheat Ridge, CO (US)

( * ) Notice: Subject to any disclaimer, the term of this patent is extended or adjusted under 35 U.S.C. 154(b) by 0 days.

(21) Appl. No.: 09/598,644

(22) Filed: Jun. 21, 2000

Related U.S. Application Data (63) Continuation-in-part of application No. 09/226,482, filed on Jan. 7, 1999, now Pat. No. 6,083,201.
(60) Provisional application No. 60/114,206, filed on Dec. 29, 1998.

(51) Int. Cl.$^7$ .................................................. A61M 1/00
(52) U.S. Cl. ........................ 604/151; 604/131; 604/186
(58) Field of Search .................................. 604/110, 121, 604/123, 131, 134, 135, 207, 151, 211, 214, 117, 157, 506, 19, 118, 132, 152, 153, 181, 186, 187, 218, 222, 226, 229

(56) References Cited

U.S. PATENT DOCUMENTS

| | | |
|---|---|---|
| 1,123,990 A | 1/1915 | Calhoun |
| 1,476,946 A | 12/1923 | Bessesen |

(List continued on next page.)

FOREIGN PATENT DOCUMENTS

| | | |
|---|---|---|
| FR | 1156298 | 5/1958 |
| FR | 2561925 | 10/1985 |
| WO | WO 91/06338 | 5/1991 |
| WO | WO 91/08002 | 6/1991 |
| WO | WO 91/16093 | 10/1991 |

*Primary Examiner*—Glenn K. Dawson
*Assistant Examiner*—Jennifer Maynard
(74) *Attorney, Agent, or Firm*—Dorr, Carson, Sloan & Birney, P.C.

(57) ABSTRACT

A multi-dose infusion pump employs a piston sliding within the internal chamber of a pump housing to dispense liquid from a port. The peripheral surface of the piston has a sequence of steps in a radial pattern spaced at intervals along the longitudinal axis of the chamber. A cap is rotatably mounted to the pump housing and includes a stop that limits forward movement of the piston by engaging a selected one of the steps on the piston at each rotational position of the cap. This causes a series of predetermined quantities of liquid to be dispensed as the cap is rotated to align the stop with each step in sequence. A spring between the cap and piston urges the piston forward in the chamber to dispense liquid from the port. The peripheral surface of the piston can also be equipped with a series of guide surfaces that allow the piston to be initially retracted toward the cap without engaging the steps while the cap is in an initial rotational position, and then guide the stop along the steps in a predetermined order as the cap is rotated through a progression of rotational positions. The forward face of the piston can also be provided with a member (e.g., a resilient diaphragm) that is compressed by fluid pressure as the piston moves forward, and then gradually returns to its initial position after forward motion of the piston stops, thereby continuing to dispense a small quantity of liquid for a period of time between doses.

18 Claims, 8 Drawing Sheets

U.S. PATENT DOCUMENTS

| | | | |
|---|---|---|---|
| 2,428,577 A | 10/1947 | Mathis | |
| 2,605,765 A | 8/1952 | Kollsman | |
| 2,792,834 A | 5/1957 | Kapelsohn | |
| 3,492,876 A | 2/1970 | Bull | |
| 3,565,292 A | 2/1971 | Jinotti | |
| 3,863,624 A | 2/1975 | Gram | |
| 3,874,382 A * | 4/1975 | Nogier et al. | 128/218 |
| 4,036,232 A | 7/1977 | Genese | |
| 4,050,459 A | 9/1977 | Sanchez | |
| 4,180,067 A | 12/1979 | Derlien | |
| 4,312,347 A | 1/1982 | Magoon | |
| 4,381,006 A | 4/1983 | Genese | |
| 4,456,152 A | 6/1984 | Young | |
| 4,467,942 A | 8/1984 | Oshikubo | |
| 4,561,856 A | 12/1985 | Cochran | |
| 4,666,430 A | 5/1987 | Brown | |
| 4,676,256 A | 6/1987 | Golden | |
| 4,765,509 A | 8/1988 | Eisenhut | |
| 4,773,900 A | 9/1988 | Cochran | |
| 4,813,937 A | 3/1989 | Vaillancourt | |
| 4,832,694 A | 5/1989 | Raphael, III | |
| 4,874,386 A | 10/1989 | O'Boyle | |
| 4,962,868 A | 10/1990 | Borchard | |
| 4,966,585 A | 10/1990 | Gangemi | |
| 4,991,742 A | 2/1991 | Chang | |
| 4,997,420 A | 3/1991 | LeFevre | |
| 5,024,661 A | 6/1991 | Wender | |
| 5,059,174 A | 10/1991 | Vaillancourt | |
| 5,062,834 A | 11/1991 | Gross | |
| 5,078,679 A | 1/1992 | Reese | |
| 5,098,385 A | 3/1992 | Walsh | |
| 5,100,389 A | 3/1992 | Vaillancourt | |
| 5,135,500 A | 8/1992 | Zdeb | |
| 5,178,609 A | 1/1993 | Ishikawa | |
| 5,178,610 A * | 1/1993 | Tsujikawa et al. | 604/132 |
| 5,290,259 A | 3/1994 | Fischer | |
| 5,318,544 A | 6/1994 | Drypen | |
| 5,346,476 A | 9/1994 | Elson | |
| 5,360,411 A | 11/1994 | Mimura | |
| 5,411,485 A | 5/1995 | Tennican | |
| 5,454,792 A | 10/1995 | Tennican | |
| RE35,192 E | 3/1996 | Reese | |
| 5,599,315 A | 2/1997 | McPhee | |
| 5,620,423 A * | 4/1997 | Eykmann et al. | 604/217 |
| 5,735,825 A * | 4/1998 | Stevens et al. | 604/218 |
| 5,897,530 A * | 4/1999 | Jackson | 604/132 |

* cited by examiner

MULTI-DOSE INFUSION PUMP PROVIDING MINIMAL FLOW BETWEEN DOSES

RELATED APPLICATIONS

The present application is a continuation-in-part of the Applicant's co-pending U.S. patent application Ser. No. 09/226,482, entitled "Multi-Dose Infusion Pump", filed on Jan. 7, 1999 now U.S. Pat No. 6,083,201. The present application is also based in part on the Applicant's U.S. Provisional Patent Application Ser. No. 60/114,206, entitled "Spring-Powered Infusion Pump", filed on Dec. 29, 1998.

BACKGROUND OF THE INVENTION

1. Field of the Invention

The present invention relates generally to the field of infusion pumps. More specifically, the present invention discloses an infusion pump capable of administering a series of dosages of liquid medication.

2. Statement of the Problem

Infusion pumps have been widely used for many years to administer antibiotics and other medications to patients. Syringe-type infusion pumps generally include a piston or plunger that slides within a housing to dispense medication. A valve or flow restrictor regulates the flow rate from the pump. Some conventional infusion pumps are driven by a spring, while other infusion pumps require manual pressure to dispense medication.

Another type of conventional infusion pump is vacuum powered. The pump consists of a fluid chamber and a vacuum chamber. Both chambers are equipped with sliding pistons that are mechanically connected (e.g., by a rod) so that a partial vacuum is created in the vacuum chamber as medication is introduced into the fluid chamber. The fluid chamber can be filled either by injecting medication under pressure, or by exerting a force on the fluid chamber piston to simultaneously draw medication into the fluid chamber and create a partial vacuum in the vacuum chamber. After the medication has been loaded into the fluid chamber, the reduced pressure in the vacuum chamber exerts pressure via the pistons and connecting rod that tends to expel medication from the fluid chamber.

Conventional infusion pumps are designed to dispense a single dose of medication, and then must be reloaded for any subsequent doses. This requires additional effort by the healthcare provider. It may entail extra expense if a new infusion pump is used for each dose, or may increase the risk of contamination if the same infusion pump is reused.

Multi-dose infusion pumps have been used in the past in the healthcare industry. However, the multi-dose infusion pumps in common use have substantial shortcomings in terms of complexity, cost, reliability, and ease of use. For example motor-driven infusion pumps can provide flexibility in terms of regulating a series of dosages to be administered to the patient, but tend to be relatively expensive and are complex to use and maintain.

When using a multi-dose infusion pump, it is desirable to continually administer a very low flow rate of medication between doses. This small continual flow, also known as the KVO (keep vein open) flow, helps to keep the patient's vein open by preventing clotting or collapse of the vein. This minimal KVO flow should be viewed in contrast to the substantially larger flow associated with a typical dose administered by a multi-dose infusion pump, in which each dose would result from a significant movement of the piston. A need currently exists for an infusion pump capable of providing such a KVO flow between doses.

3. Prior Art

Multi-dose infusion pumps, syringes, and related fluid-dispensing devices that have been used in the past include the following:

| Inventor | | Patent No. | Issue Date |
|---|---|---|---|
| Drypen et al. | | 5,318,544 | June 7, 1994 |
| Ishikawa | | 5,178,609 | Jan. 12, 1993 |
| Zdeb | | 5,135,500 | Aug. 4, 1992 |
| Wender et al. | | 5,024,661 | June 18, 1991 |
| LeFevre | | 4,997,420 | March 5, 1991 |
| Chang | | 4,991,742 | Feb. 12, 1991 |
| Gangemi | | 4,966,585 | Oct. 30, 1990 |
| Borchard | | 4,962,868 | Oct. 16, 1990 |
| Raphael et al. | | 4,832,694 | May 23, 1989 |
| Vaillancourt | | 4,813,937 | Mar. 21, 1989 |
| | France | 2,561,925 | Oct. 4, 1985 |
| Oshikubo | | 4,467,942 | Aug. 28, 1984 |
| Sanchez | | 4,050,459 | Sep. 27, 1977 |
| Bull et al. | | 3,492,876 | Feb. 3, 1970 |
| | France | 1,156,298 | May 14, 1958 |
| Kapelsohn | | 2,792,834 | May 21, 1957 |
| Mathis | | 2,428,577 | Oct. 7, 1947 |

Drypen et al. disclose a metering syringe with a plunger having a series of stop surfaces spaced along its length that contact a stop on the syringe tube. The stop surfaces halt forward movement of the plunger at predetermined intervals. The stop surfaces are angularly displaced about the longitudinal axis of the plunger, so that incremental rotation of the plunger permits the plunger to be advanced to the next stop surface.

Ishikawa discloses a medical liquid injector for continuous transfusion that includes a syringe fitted with a piston having a detachable shaft rod, and a cap that can be connected to the proximal end of the syringe. The cap has an elastic pressing device (i.e., a spring) for continuously pressing the piston (after the shaft rod has been removed).

Zdeb discloses an example of a vacuum-powered infusion pump.

Wender et al. disclose a hypodermic syringe having a plunger shaft with a series of horizontal locking grooves. These grooves halt forward movement of the plunger within the syringe barrel at predetermined intervals. At each stop, the plunger must be rotated by 180 degrees to proceed to the next stop.

LeFevre, Gangemi, and Chang disclose examples of spring-powered infusion pumps.

Borchard discloses an apparatus for dispensing a controlled dose of liquid medication that includes a dispenser head which fits over the needle-end of a syringe, and a tube slidably engaged to the dispenser head which encases the piston-end of the syringe. Sliding the tube forward pushes the syringe piston and thereby dispenses liquid from the syringe. The amount of liquid dispensed can be controlled by the pin and slot arrangement between the dispenser head and tube shown in FIGS. 3a and 3b of the Borchard patent.

Raphael et al. disclose a programmed action hypodermic syringe having at least one pin protruding into the bore of the barrel that slidably engages a tracking groove in the plunger.

Vaillancourt discloses an infusion pump powered by an elastomeric bladder.

French Patent No. 2,561,925 discloses a syringe for dispensing a series of doses of medication. As shown in FIGS. 2–5 of this patent, a pin and slot arrangement between the syringe barrel and piston limits the forward motion of the syringe piston and thereby determines the size of each dose. The embodiment shown in FIG. 3 of this patent uses a slot with a series of steps. This embodiment would require that the piston be rotated slightly before dispensing the next dose.

Oshikubo discloses a repeating liquid dispenser having a tubular main body, an actuating member slidably disposed in the main body, and a pressure button on the end of the actuating member projecting out of the upper end of the main body. A spring-loaded rack and pawl mechanism is used to incrementally dispense a quantity of liquid each time that the actuating member is depressed.

Sanchez discloses a hypodermic syringe for administering a plurality of measured doses that includes a barrel and plunger. The size of each dose is controlled by a pin and track mechanism between the barrel and plunger. The track has a plurality of steps controlling forward motion of the plunger within the barrel.

Bull et al. disclose an aliquant discharge device having a syringe with a plunger and a side arm in the upper section of the syringe barrel. In use, the plunger is withdrawn beyond the side arm and suction draws up a blood sample into the syringe. The plunger is then depressed cutting off the vacuum and trapping a known amount of blood in the syringe barrel. This blood specimen is then aliquoted by means of metal stops affixed to the upper end of the plunger that abut on a series of steps as shown in FIGS. 3A–3E of Bull et al.

French Patent No. 1,156,298 discloses another example of a hypodermic syringe with a track mechanism having a series of steps for controlling forward motion of the syringe piston.

Kapelsohn discloses another example of a syringe with a pin and track mechanism to fix the amount of liquid dispensed.

Mathis discloses a liquid-measuring dispenser with a pin and track mechanism for controlling the amount of liquid dispensed.

The prior art relating to the KVO flow includes the following:

| Inventor | Patent No. | Issue Date |
| --- | --- | --- |
| Racz | 5,722,955 | March 3, 1998 |
| Webb | 4,333,456 | June 8, 1982 |
| Binard et al. | 4,240,430 | Dec. 23, 1980 |
| Binard et al. | 4,074,714 | Feb. 21, 1978 |
| Leibinsohn | 4,064,879 | Dec. 27, 1977 |
| Binard et al. | 4,030,497 | June 21, 1977 |
| Binard et al. | 4,000,741 | Jan. 4, 1977 |
| Dawe | 3,998,223 | Dec. 21, 1976 |

Dawe discloses a syringe having a plunger with a resilient balloon-like diaphragm that stretches to provide a more even pressure as fluid is dispensed. The diaphragm also serves as a visual indicator of over-pressure that might damage the vein.

Binard et al. disclose a syringe having an external flexible balloon in fluid communication with the fluid chamber of the syringe, or a resilient diaphragm within the fluid chamber. The balloon inflates at a predetermined pressure to relieve excessive pressure within the syringe and to provide a visual indicator of over-pressure. Similarly, in the embodiments employing an internal diaphragm, the diaphragm deforms at a predetermined pressure to relieve excessive pressure and to provide a visual indicator of over-pressure.

Leibinsohn discloses a pressure-indicating syringe with a telescoping or collapsible plunger.

Webb discloses a self-aspirating syringe for use in combination with a cartridge ampoule having a rubber diaphragm at its lower end and a slidable rubber piston at its upper end.

Racz discloses a pressure-sensing syringe having a piece of compressible material attached to the face of the piston to provide a visual indicator of the pressure within the fluid chamber of the syringe.

4. Solution to the Problem

None of the prior art references discussed above show a multi-dose infusion pump that provides a KVO function. In particular, the present invention discloses a multi-dose infusion pump having a member (e.g., a resilient diaphragm) extending across the face of the piston that is compressed rearward by pressure within the fluid chamber as the piston moves forward and fluid is dispensed, and then gradually returns to its initial position after forward motion of the piston stops to continue to dispense a small quantity of fluid for a period of time.

SUMMARY OF THE INVENTION

This invention provides a multi-dose infusion pump that employs a piston sliding within the internal chamber of a pump housing to dispense liquid from a port. The peripheral surface of the piston has a sequence of steps in a radial pattern spaced at intervals along the longitudinal axis of the chamber. A cap is rotatably mounted to the pump housing and includes a stop that limits forward movement of the piston by engaging a selected one of the steps on the piston at each rotational position of the cap. This causes a series of predetermined quantities of liquid to be dispensed as the cap is rotated to align the stop with each step in sequence. A spring between the cap and piston urges the piston forward in the chamber to dispense liquid from the port. The peripheral surface of the piston can also be equipped with a series of guide surfaces that allow the piston to be fully retracted toward the cap without engaging the steps while the cap is in an initial rotational position, and then guide the stop along the steps in a predetermined order as the cap is rotated through a progression of rotational positions. The forward face of the piston can also be provided with a member (e.g., a resilient diaphragm) that is compressed under fluid pressure as the piston moves forward, and then gradually returns to its initial position after forward motion of the piston stops, thereby continuing to dispense a small quantity of liquid for a period of time between doses.

A primary object of the present invention is to provide a multi-dose infusion pump that is inexpensive to produce.

Another object of the present invention is to provide a multi-dose infusion pump that can be easily used by a healthcare provider with minimal instruction.

Another object of the present invention is to provide an infusion pump capable of providing a minimal continuing flow between doses to help keep the patient's vein open.

These and other advantages, features, and objects of the present invention will be more readily understood in view of the following detailed description and the drawings.

BRIEF DESCRIPTION OF THE DRAWINGS

The present invention can be more readily understood in conjunction with the accompanying drawings, in which.

DETAILED DESCRIPTION OF THE INVENTION

Figure 1:
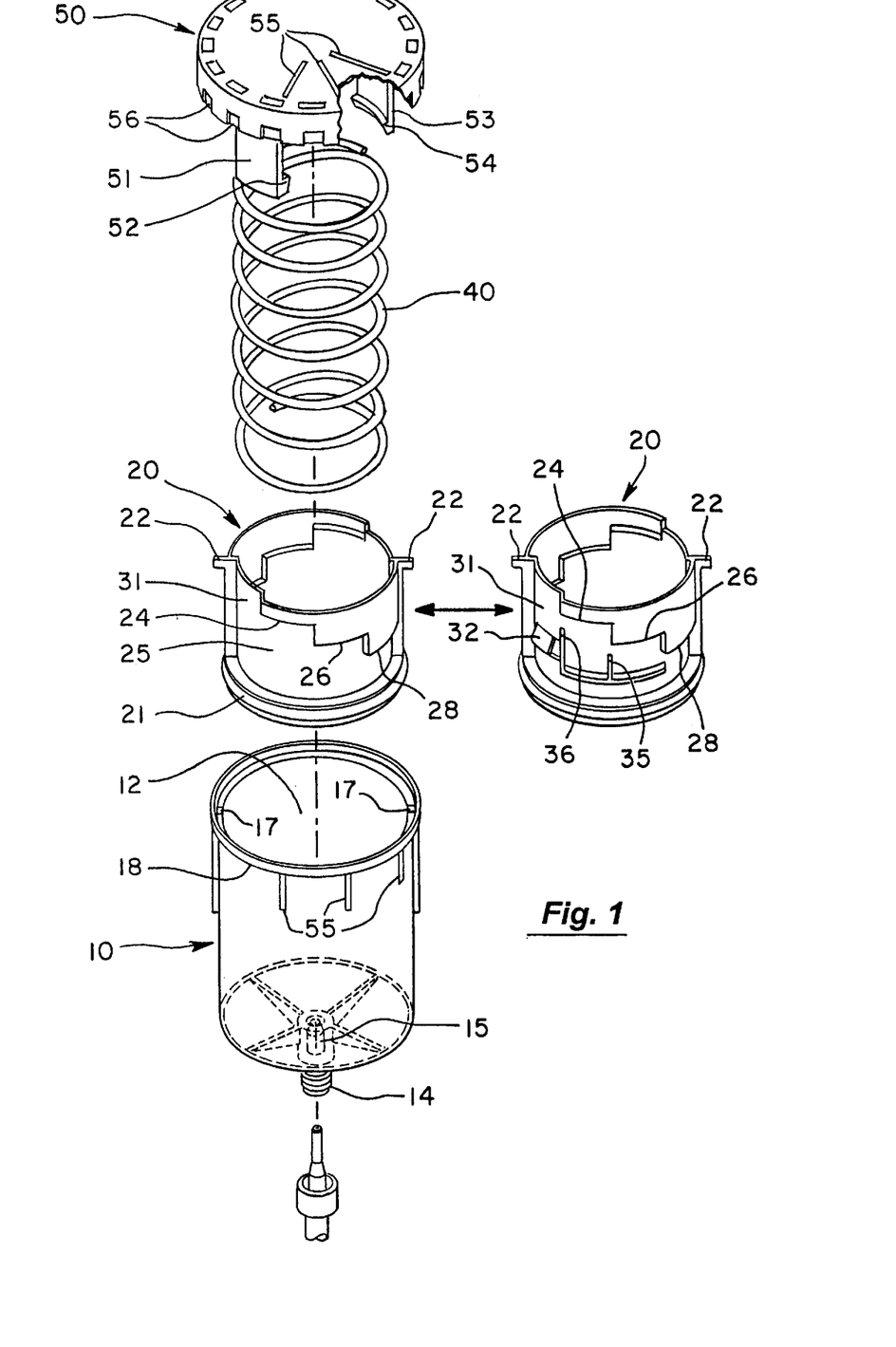
FIG. 1 is an exploded perspective view of the present infusion pump.
Figure 2:
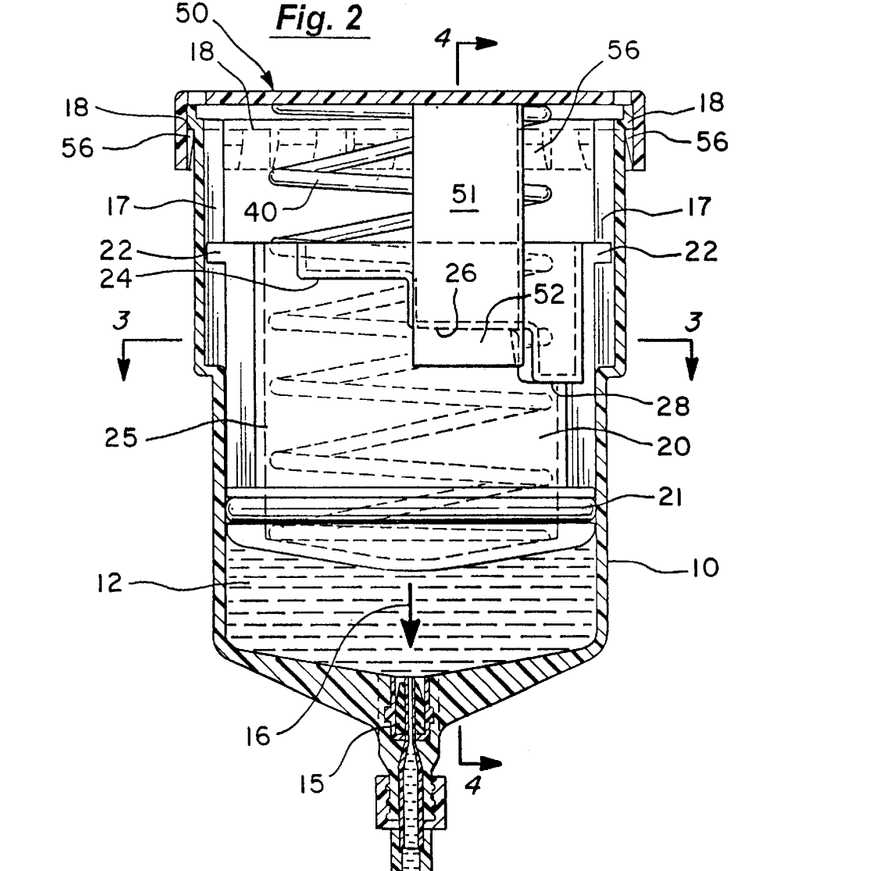
FIG. 2 is a vertical cross-sectional view of the assembled infusion pump.
Figure 3:
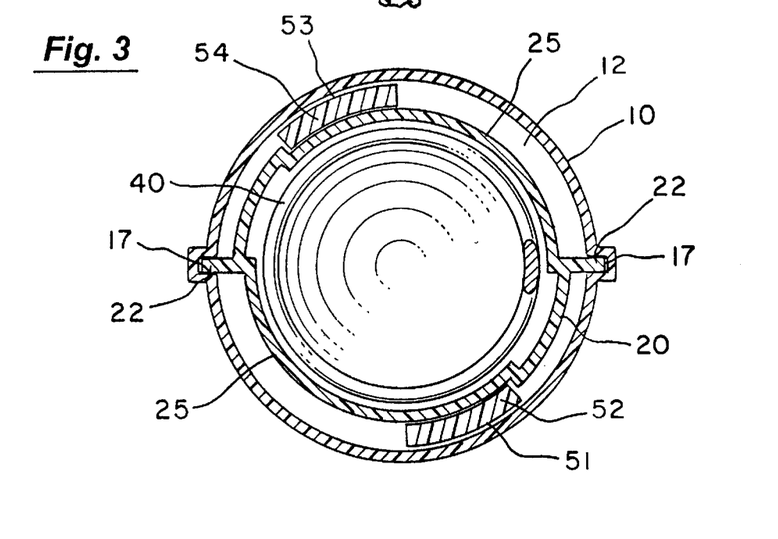
FIG. 3 is a horizontal cross-sectional view of the infusion pump corresponding to FIG. 2 taken along lines 3—3.
Figure 4:
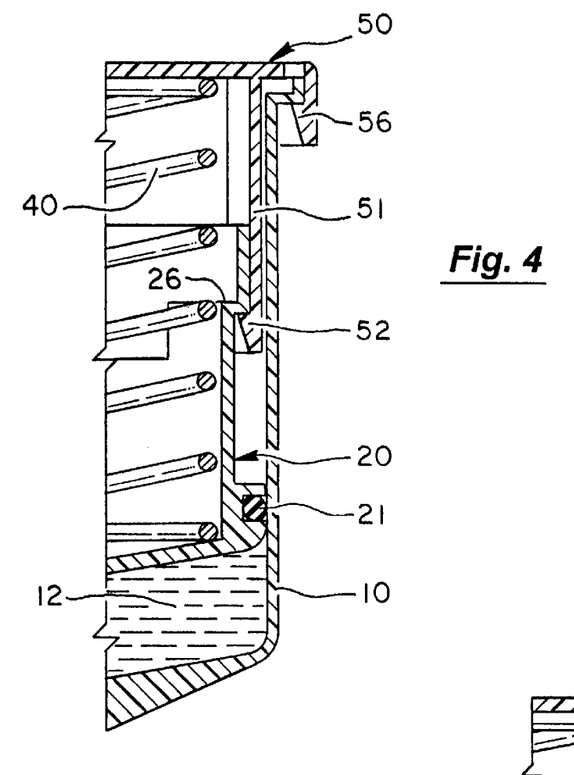
FIG. 4 is a detail vertical cross-sectional view corresponding to FIG. 2 taken along lines 4—4 showing a stop 52 extending from the cap 50 and contacting one of the steps 26 on the piston 20.

Turning to FIG. 1, an exploded perspective view is provided of the present invention. FIGS. 2 through 4 are corresponding cross-sectional views of the assembled infusion pump. The infusion pump includes a pump housing 10, which has an internal chamber 12 extending along a longitudinal axis from a proximal opening to a distal port 14 used for dispensing liquid from the chamber 12.

A piston 20 slidably engages the internal chamber 12 of the pump housing 10. An O-ring 21 extending about the periphery of the piston maintains a fluid-tight seal against the wall of the pump housing 10. Thus, the piston 20 and pump housing 10 together define an enclosed region suitable for containing a quantity of a liquid medication or fluid. The chamber 12 of the pump housing 10 is typically cylindrical, although other shapes could be readily substituted, provided the piston has a complementary cross-section to maintain a fluid-tight seal.

Liquid can be dispensed through the port 14 of the chamber 12 by sliding the piston forward along the longitudinal axis 16, as illustrated in FIG. 2. The port 14 includes a duck-bill valve 15 that prevents liquid from escaping from the chamber 12 while the infusion pump is not in use. An infusion connector can be inserted through the duck-bill valve 15, as shown in FIG. 2, to create an opening that allows liquid to flow from the chamber 12 through the connector and tubing leading to the patient.

Figure 5:
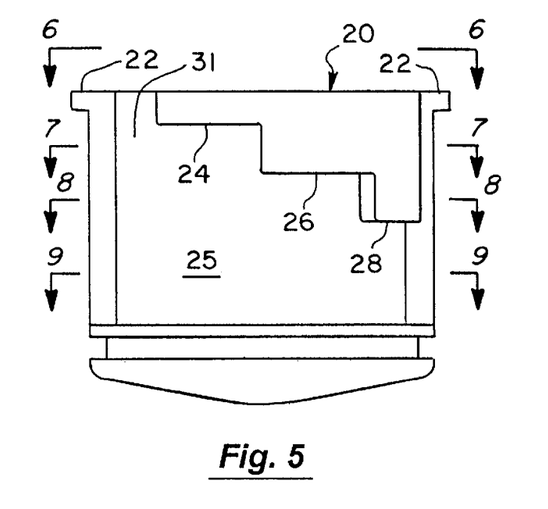
FIG. 5 is a side elevational view of the piston 20.
Figure 6:
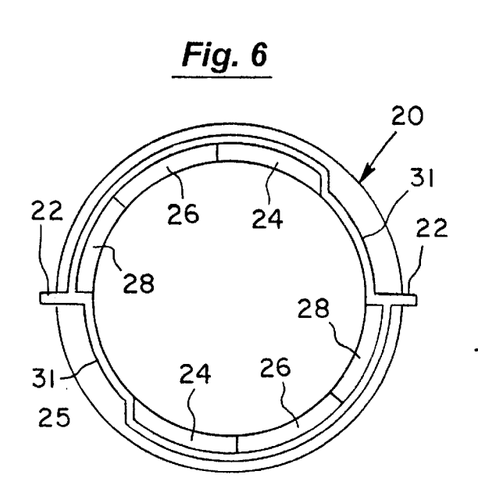
FIG. 6 is a horizontal cross-sectional view of the piston 20 corresponding to FIG. 5 taken along lines 6—6.
Figure 7:
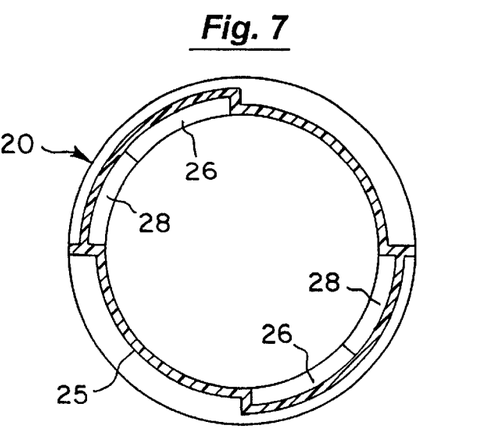
FIG. 7 is a horizontal cross-sectional view of the piston corresponding to FIG. 5 taken along lines 7—7.
Figure 8:
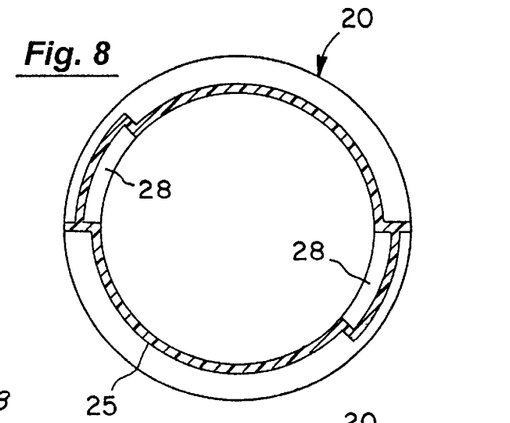
FIG. 8 is a horizontal cross-sectional view of the piston corresponding to FIG. 5 taken along lines 8—8.
Figure 9:
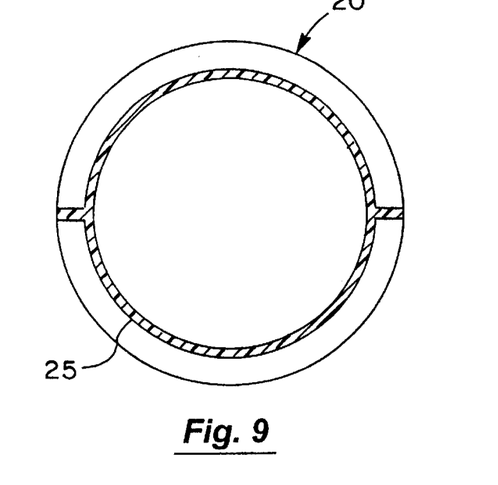
FIG. 9 is a horizontal cross-sectional view of the piston corresponding to FIG. 5 taken along lines 9—9.

FIG. 5 is a side elevational view of the piston 20. FIGS. 6 through 9 are corresponding horizontal cross-sectional views of the piston 20 at various elevations. The piston 20 has a peripheral surface 25 above the O-ring 21 with a progression of raised steps 24, 26, and 28 spaced at intervals in a radial pattern on the peripheral surface 25 of the piston 20. Two tabs 22 extend radially outward from the peripheral surface 25 of the piston 20 to engage corresponding longitudinal slots 17 in the wall of the pump housing 10, as depicted in FIG. 3. These tabs 22 guide the piston 20 so that it can slide along the longitudinal axis 16 within the pump housing 10 and also prevent the piston 20 from rotating with respect to the pump housing 10.

A cap 50 is rotatably mounted over the proximal opening of the pump housing 10, as shown in FIG. 2. For example, the cap can be equipped with a series of tabs 56 that engage the lip 18 extending around the periphery of the proximal opening of the pump housing 10, shown in FIGS. 2 and 4. The tabs 56 initially clip over the lip 18 of the pump housing when the device is being assembled. However, it is very difficult to subsequently remove the cap 50 from the pump housing 10. The tabs 56 on the cap 50 slide freely relative to the lip 18 on the pump housing 10. This allows the user to easily rotate the cap 50 with respect to the pump housing 10 about the longitudinal axis 16.

A spring 40 compressed between the cap 50 and the rear faie of the piston 20 urges the piston 20 forward along the longitudinal axis 16 toward the distal port 14. The volume of liquid dispensed is determined by the degree of forward motion of the piston 20. In particular, the volume dispensed is equal to the cross-sectional area of the piston multiplied by the distance that the piston moves in the axial direction. The flow rate can be controlled by a flow restrictor or valve (not shown) in the tubing downstream from the infusion connector attached to the port 14.

The cap 50 has a number of arms 51, 53 that extend axially forward between the interior surface of the pump housing 10 and the peripheral surface 25 of the piston 20. In the embodiment of the present invention shown in the drawings, the cap 50 has two diametrically-opposed arms, although any number of other configurations could be substituted. A stop 52, 54 extends radially inward from the distal end of each arm 51, 53. Each stop engages a selected one of the raised steps 24, 26, or 28 at each of a plurality of rotational positions of the cap 50. The selected step 24, 26, or 28 then limits forward axial movement of the piston 20 within the chamber 12 to dispense a predetermined quantity of liquid. A series of visual indicia 55 on the cap 50 and outer surface of the pump housing 10 show the proper rotational positions of the cap to align the stops 52, 54 with each of the steps 24–28.

The number of sets of steps 24–28 on the piston 20 typically corresponds to the number of arms 51, 53 and stops 52, 54 extending from the cap 50, so that each stop will engage one set of steps. Thus, the embodiment shown in the drawings has two sets of steps 24–28 located in a diametrically-opposing arrangement on the peripheral surface 25 of the piston 20. In contrast, the number of steps 24–28 in each set is entirely a matter of design choice determined by the number and quantity of dosages that are desired.

The present invention enables a healthcare provider to administer medication to a patient in a series of doses over time from a single infusion pump. By rotating the cap 50, the healthcare provider determines which of the raised steps 24–28 will be engaged by the cap stops 52, 54 as the piston 20 is pushed forward by the spring 40. This limits the range of forward motion of the piston 20 relative to the cap 50, and therefore determines the volume of medication to be dispensed for each rotational position of the cap 50.

The chamber 12 of the infusion pump is initially loaded with medication by the manufacturer or a healthcare provider. The device is assembled with the piston 20 disposed within the pump housing 10 and the spring 40 compressed between the piston 20 and the cap 50. The healthcare provider then connects tubing with an infuser connector to the distal port 14 of the infusion pump, as illustrated in FIG. 2. Pressurized fluid is fed through the tubing into the fluid chamber 12 with sufficient pressure to open the duck-bill valve 15 and overcome the force of the spring 40. Once the pump chamber 12 is filled to a predetermined level, the tubing and infuser connector are removed and the duck-bills of the duck-bill valve 15 return to their sealed position to retain the fluid within the pump chamber 12.

The liquid medication is retained by the duck-bill valve 15 until the infusion pump is ready for use, at which time, tubing with an infuser connector is connected to the distal port 14 of the infusion pump, and the fluid is allowed to flow from the pump chamber 12 as shown in FIG. 2. The device can be filled with a syringe or any other positive-pressure fluid source.

The healthcare provider can select a first dosage by rotating the cap 50 so that each stop 52, 54 is axially aligned with the first raised step 28. This first dosage will then be dispensed through the port 14 as the piston 20 moves forward from its initial, fully-retracted position until the stop 52, 54 comes into contact with the first raised step 28 on the piston 20. At that point, the piston 20 is restrained from further forward movement by the stop 52, 54 and no further liquid is dispensed. The healthcare provider can continue with a second dosage by rotating the cap 50 so that each stop 52, 54 is aligned with the second raised step 26. The second dosage is determined by the incremental distance between the first and second steps 28 and 26 (multiplied by the cross-sectional area of the piston). Similarly, the healthcare provider can continue with a third dosage by rotating the cap 50 so that each stop 52, 54 is aligned with the third step 24. Again, the third dosage is determined by the incremental distance between the second and third steps 26 and 24. Finally, a fourth dosage can be selected by rotating the cap 50 so that the stop 52, 54 is not aligned with any of the steps 24–28. In other words, the stop 52, 54 slides along the longitudinal guide slot 31 without contacting any of the steps 24–26. This allows the piston 20 to move forward until it contacts the distal wall of the chamber 12 and all of the liquid has been dispensed.

For example, the infusion pump can be initially filled with 400 ml of medication. The cap 50 is initially turned to a first rotational position, which will cause the cap stops 52, 54 to engage a first set of raised steps 28 after 100 ml have been dispensed. The cap can subsequently be rotated to a second rotational position, which will cause the cap stops 52, 54 to engage a second set of raised steps 26 after a second 100 ml have been dispensed. If desired, this process can be repeated two more times to dispense the remaining 200 ml in two 100 ml increments.

The preceding discussion has assumed that the infusion pump will be used to dispense a series of dosages in a predetermined sequence. However, the healthcare provider also has the option of using any single step or any progression of steps. The healthcare provider can rotate the cap to align the stops 52, 54 with any of the steps 24–28. For example, the healthcare provider can dispense a volume of medication equal to both the first and second dosages by rotating the cap to align the stops 52, 54 directly with the second step 26.

Figure 10:
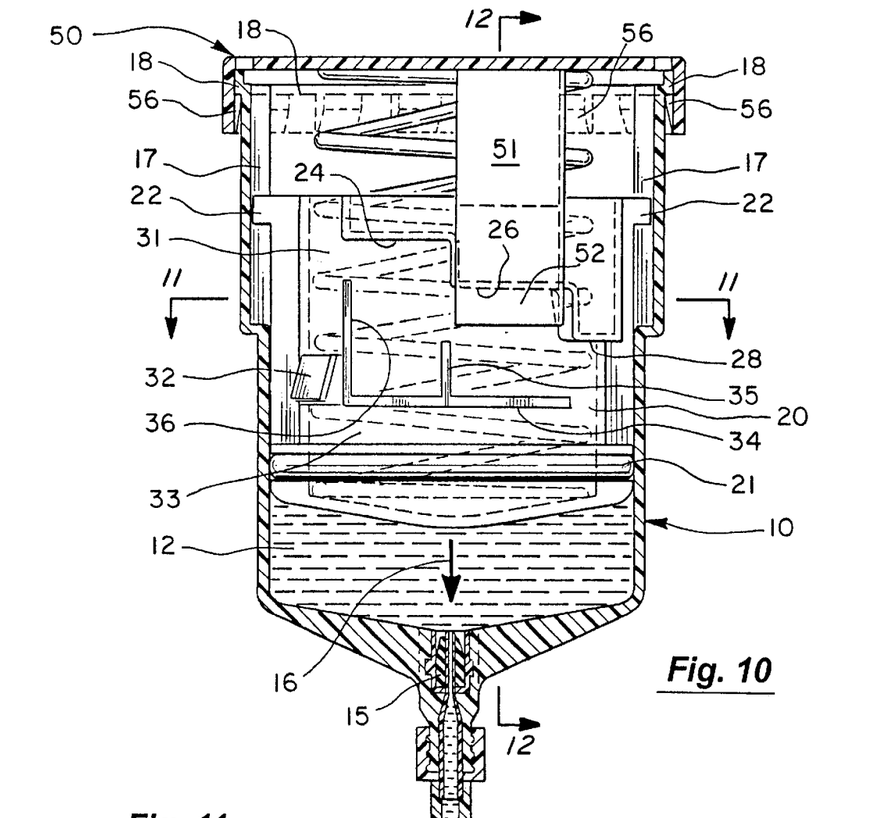
FIG. 10 is a vertical cross-sectional view of a second embodiment of the infusion pump employing a piston with a series of guides on the peripheral surface of the piston guiding the stop extending from the cap along the steps on the piston in a predetermined order.
Figure 11:
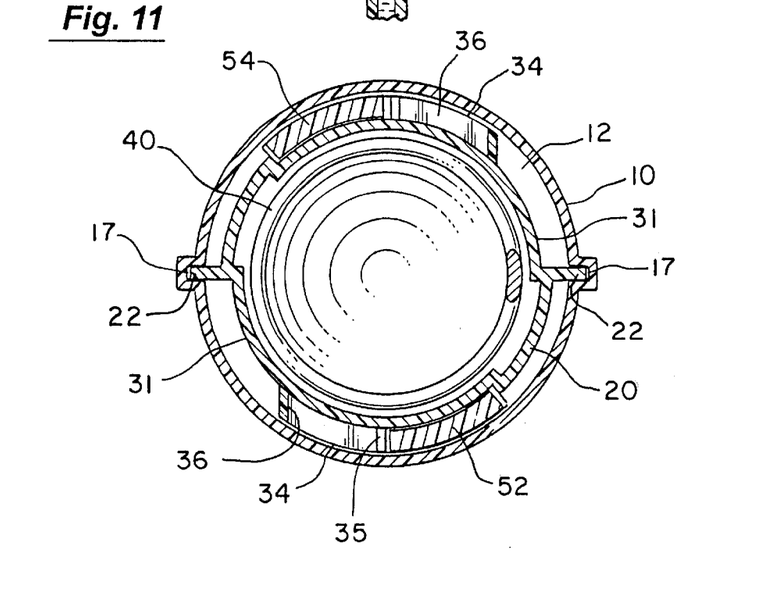
FIG. 11 is a horizontal cross-sectional view of the infusion pump corresponding to FIG. 10 taken along lines 11—11.
Figure 12:
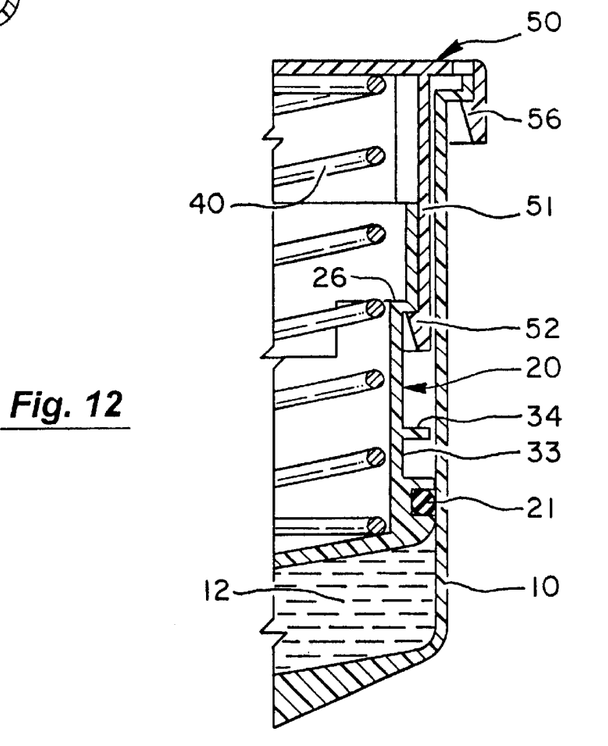
FIG. 12 is a detailed vertical cross-sectional view corresponding to FIG. 10 taken along lines 12—12, showing a stop 52 extending from the cap 50 and contacting one of the steps 26 on the piston 20.
Figure 13:
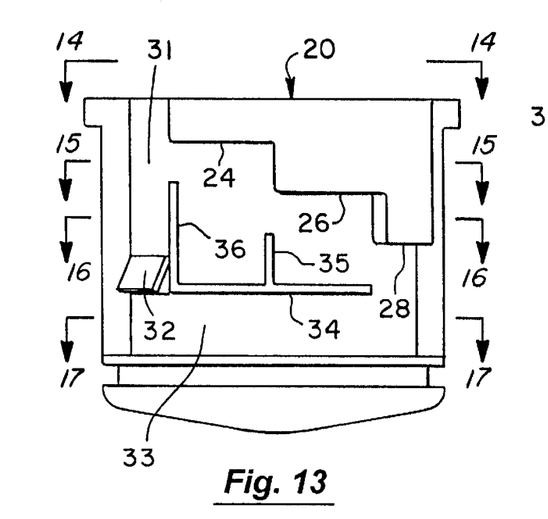
FIG. 13 is a side elevational view of the second embodiment of the piston 20.
Figure 14:
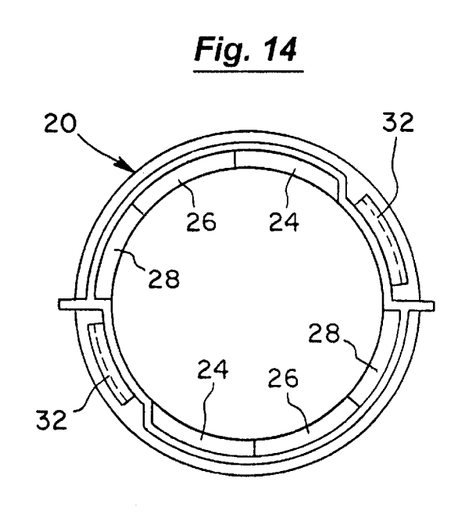
FIG. 14 is a horizontal cross-sectional view of the second embodiment of the piston 20 corresponding to FIG. 13 taken along lines 14—14.
Figure 15:
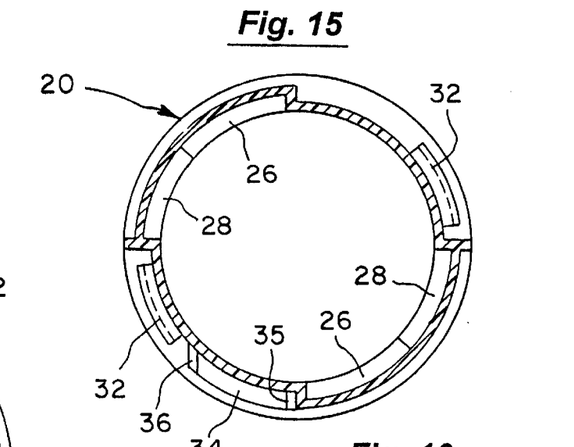
FIG. 15 is a horizontal cross-sectional view of the second embodiment of the piston 20 corresponding to FIG. 13 taken along lines 15—15.
Figure 16:
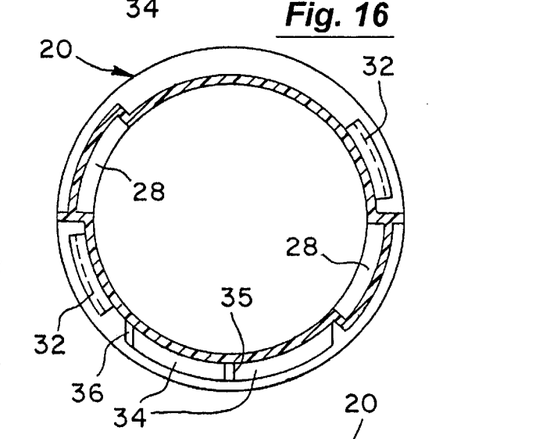
FIG. 16 is a horizontal cross-sectional view of the second embodiment of the piston 20 corresponding to FIG. 13 taken along lines 16—16.
Figure 17:
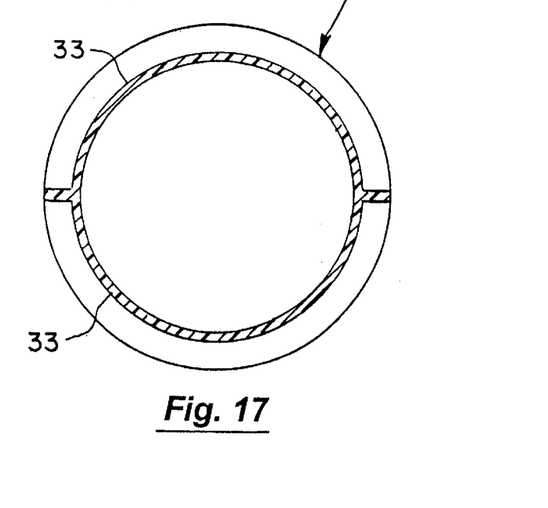
FIG. 17 is a horizontal cross-sectional view of the second embodiment of the piston 20 corresponding to FIG. 13 taken along lines 17—17.

A second embodiment of the infusion pump is shown in FIGS. 10–17 having a series of guides 34, 35, and 36 on the peripheral surface 25 of the piston 20 forward of the raised steps 24–28. In the first embodiment, there is nothing to prevent the entire dose of medication from being accidentally administered at once by rotating the cap 50 directly to the fourth rotational position. The guides 34–36 are intended to prevent this by guiding and limiting the path of the cap stops 52, 54 through each of the rotational positions in proper sequence. FIG. 10 is a vertical cross-sectional view of a second embodiment of the piston. FIGS. 11 and 12 are corresponding horizontal and vertical cross-sectional views. FIG. 13 is a side elevational view of the second embodiment of the piston 20. FIGS. 14–17 are corresponding horizontal cross-sectional views at various elevations.

In this second embodiment, each cap stop 52, 54 is initially aligned with a longitudinal guide slot 31 (see FIGS. 10 and 13) that allows the piston 20 to be fully retracted within the piston housing 10 as liquid is loaded under pressure into the chamber 12. As this occurs, each cap stop 52, 54 passes over an angled tab 32 in the longitudinal guide slot 31. The angled tab 32 allows the piston 20 to be freely retracted, but prevents the cap stop 52, 54 from being withdrawn via the longitudinal guide slot 31. This prevents the entire contents of the pump chamber 12 from accidentally being dispensed at one time. Instead, the healthcare provider must rotate the cap 50 so that the cap stop 52, 54 slides along a circumferential guide slot 33 (defined by a circumferential guide 34) until the stop 52, 54 is aligned with the first step 28. At this point, the piston 20 can move forward under pressure from the spring 40 until the stop 52, 54 comes into contact with the first step 28. The dosage of medication dispensed is proportional to the axial distance between the distal edge of the circumferential guide 34 and the first step 28.

After the first dose has been dispensed, the healthcare provider can dispense a second dose by rotating the cap 50 until the edge of the cap stop 52, 54 contacts the shorter longitudinal guide segment 35. This ensures that the stop 52, 54 is in axial alignment with the second step 26. At his point, the piston 20 moves forward once more until the stop 52, 54 comes into contact with the second step 26.

After the second dose has been dispensed, the healthcare provider can dispense a third dose by the rotating the cap 50 until the edge of the cap stop 52, 54 contacts the longer longitudinal guide segment 36. This moves the stop 52, 54 into axial alignment with the third step 24. The spring 40 can then move the piston 20 forward until the stop 52, 54 contacts the third step 24.

Finally, the healthcare provider can dispense the remaining liquid in the chamber 12 by rotating the cap 50 until the cap stop 52, 54 slides past the proximal end of the longer longitudinal guide segment 36 and returns to the longitudinal guide slot 31 above the angled tab 32. This allows the piston to move forward until the pump chamber 12 is completely emptied.

It should be expressly understood that there are a wide range of possible variations based on the basic concept described above. For example, other drive means could be substituted for the coil spring shown in the drawings. Other types of springs or elastomeric materials could be used. Alternatively, the infusion pump could be manually actuated, or vacuum powered as disclosed by U.S. Pat. No. 5,135,500 (Zdeb).

As mentioned previously, the number of piston steps 24–28 and their spacing along the longitudinal axis of the piston 20 can be designed to provide a variety of dose configurations. The number of steps 24–28 determine the maximum number of doses that can be dispensed without reloading the infusion pump. For example, a piston with one step can be used to dispense up to two doses. A piston with two steps can be used to dispense up to three doses. In general, a piston with N steps can be used to dispense up to N+1 doses.

In another embodiment, the raised steps 24–28 and guides 34–36 could protrude radially inward from the inside peripheral surface of the piston 20. The diameter between the arms 51, 53 extending forward from the cap 50 would be slightly smaller. The stops 52, 54 at the ends of the cap arms 51, 53 would point radially outward, rather than inward as shown in the figures. This embodiment would have the advantage of reducing any risk that the medication might leak and come into contact with the steps 24–28, guides 34–36, or the components of the cap 50 that could result in contamination.

In another embodiment, the placement of the piston steps 24–28 and cap stops 52, 54 could be reversed. The cap 50 can be equipped with a progression of inwardly-protruding steps that engage one or more stops extending outward from the peripheral surface 25 of the piston 20.

In yet another embodiment, the raised steps 24–28 could be replaced with grooves and/or steps that are recessed to varying degrees into the peripheral surface 25 of the piston 20. The cap arms 51, 53 would slide over the peripheral surface 25 of the piston, while the stops 52, 54 at the ends of the cap arms 51, 53 track the recessed grooves or steps.

Figure 18A:
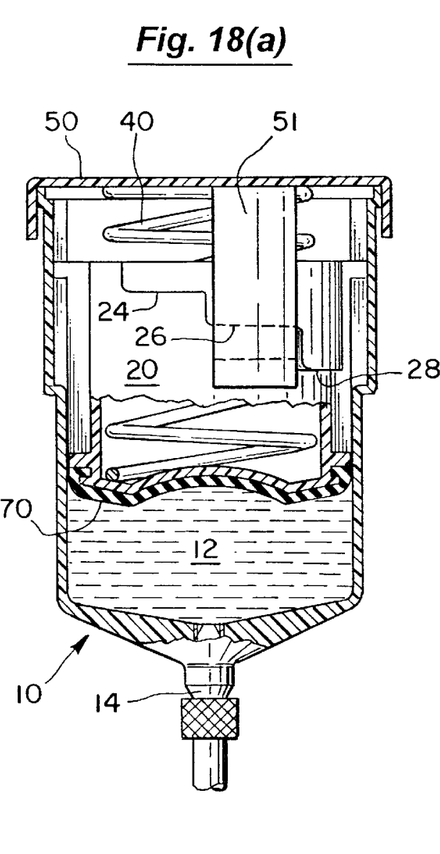
FIGS. 18(a) through 18(c) are three cross-sectional views of an embodiment of the present infusion pump equipped with a resilient member 70 extending across the face of the piston 20 to provide a KVO function.
Figure 18B:
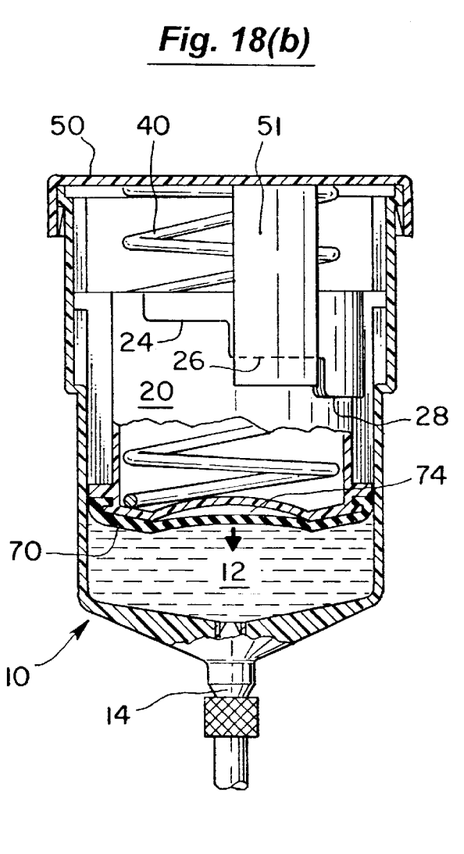
Figure 18C:
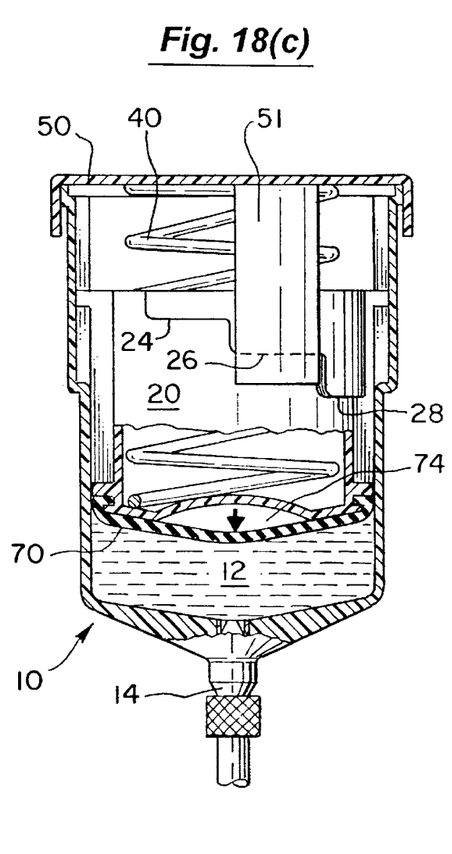

Keep Vein Open (KVO) Function. FIGS. 18(a) through 18(c) are three cross-sectional views of an embodiment of the present infusion pump equipped with a resilient member 70 extending across the face of the piston 20 to provide a KVO flow between doses. As previously discussed, the infusion pump includes a pump housing 10, which has an internal chamber 12 and a port 14 for dispensing liquid from the chamber 12. A piston 20 slidably engages the internal chamber 12 of the pump housing 10 to dispense liquid from the chamber 12 through the port 14. A flow restrictor 15 (e.g., a duck-bill valve) restricts the flow of liquid from the chamber 12 through the port 14, thereby maintaining pressure within the chamber 12 as liquid is dispensed.

In this embodiment, a member 70 covers at least a portion of the forward face of the piston 20. For example, the member 70 can be a resilient diaphragm having a substantially convex cross-sectional shape, as depicted in FIG. 18(c). The resilient member 70 can be made of silicone, rubber, plastic, or other suitable flexible materials. In the embodiment shown in FIGS. 18(a)–18(c), the resilient member 70 covers the entire face of the piston 20 and is secured around the periphery of the piston to define an enclosed, fluid-tight region 74 between the forward face of the piston 20 and resilient member 70. Alternatively, the region behind the resilient member 70 can be open to the atmosphere. For example, this can be accomplished by using a piston having vent openings or an incomplete piston face that allows air pressure equalization between the region behind the resilient member 70 and the region behind the piston.

As the piston 20 moves forward to dispense fluid from the chamber 12, the flow restrictor 15 restricts the flow from the chamber 12 and increases the pressure within the chamber 12. This increased pressure causes the resilient member 70 to move rearward from its initial position, compressing the enclosed region 74 behind the resilient member 70. The air trapped in the enclosed region acts as a spring, supplementing the resisting force provided by the resilient member 70. Depending on the volume of the enclosed region, the resilient member 70 can be almost completely flattened against the face of the piston 20 as shown in FIG. 18(a).

After forward motion of the piston 20 stops at the end of the dose, the pressure within the chamber 12 gradually drops and the resilient member 70 begins to return to its initial position, as shown in FIG. 18(b). This gradual forward motion of the resilient member 70 can continue for many minutes, or several hours, depending on the dimensions and shape of the resilient member 70, and the elastic properties of the material selected for the resilient member 70. Throughout this period, a small continuous flow of fluid is driven from the chamber 12 by gradual forward movement of the resilient member 70. Eventually, the resilient member returns to its initial position, as shown in FIG. 18(c).

This process can then be repeated when the next dose is administered. In the case of a multi-dose infusion pump, each dose would result from a significant movement of the piston (i.e., from one step on the piston to the next step). In contrast, the KVO flow is provided by gradual return of the resilient member 70 to its initial position following each dose.

Figure 19A:
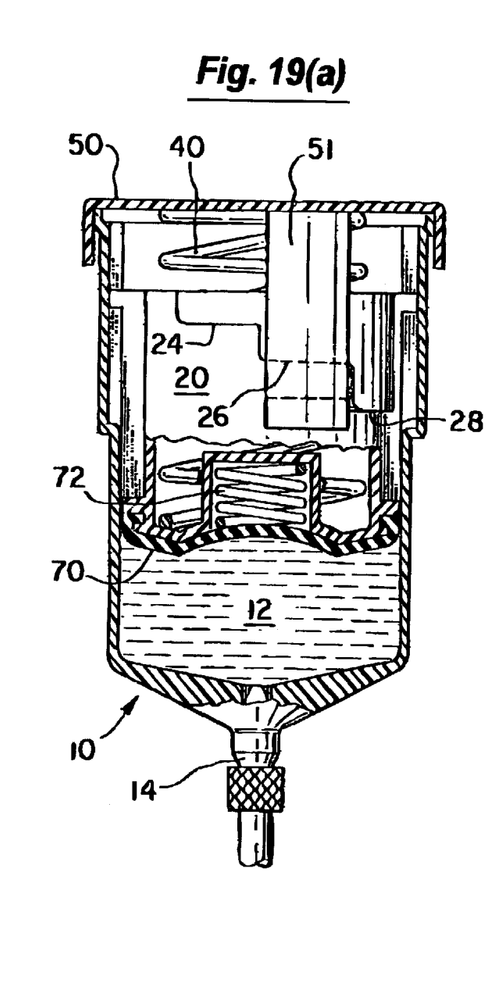
FIGS. 19(a) through 19(c) are three cross-sectional views of another embodiment of the present infusion pump using a secondary spring 72 to assist the resilient member 70 in producing a KVO flow between doses.
Figure 19B:
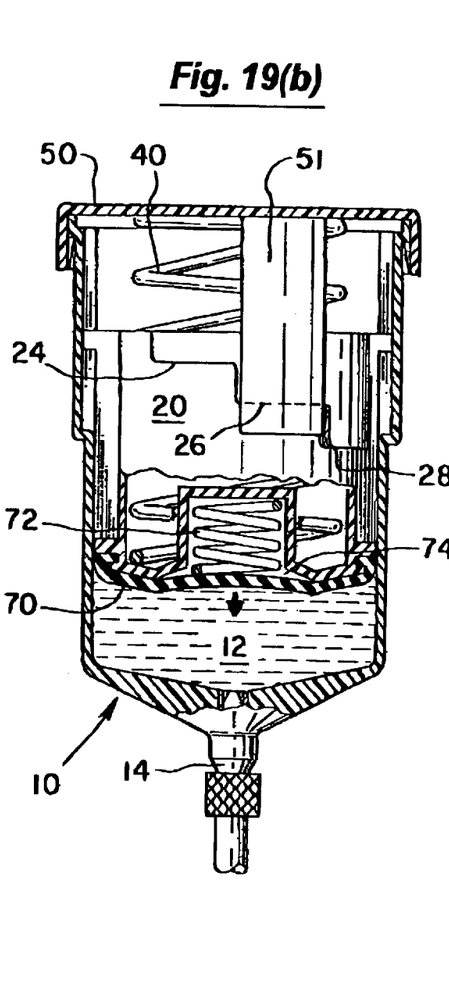
Figure 19C:
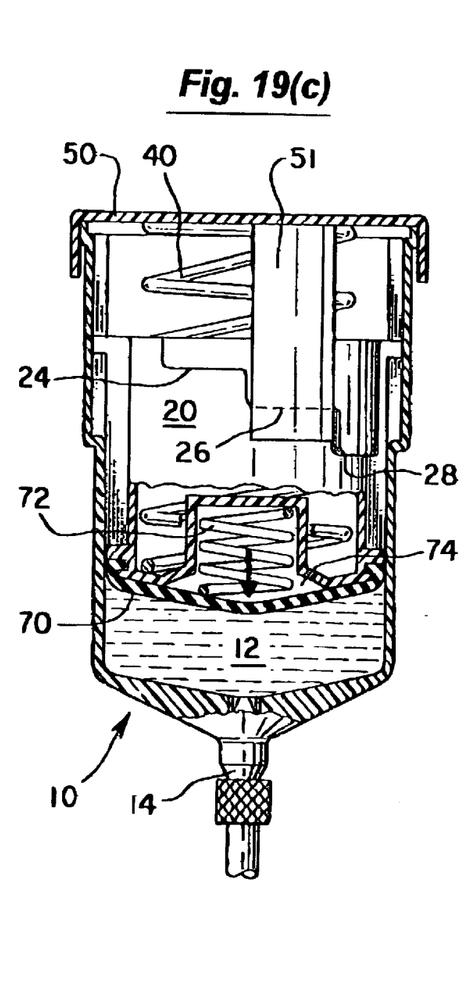

FIGS. 19(a) through 19(c) are three cross-sectional views of another embodiment of the present infusion pump using a secondary spring 72 to assist the resilient member 70 in producing a KVO flow between doses. In the embodiment illustrated in FIGS. 18(a)–18(c), the resiliency and shape of the resilient member 70 serves as a kind of spring that returns the resilient member 70 to its initial form. Here, the secondary spring 72 provides a supplementary force to that of the resilient member 70. In FIG. 19(a), the secondary spring 72 is also compressed and exerts a resisting force as the resilient member 70 is pressed against the face of the piston 20 by the fluid pressure. As shown in FIGS. 19(b) and 19(c), the secondary spring 72 then gradually expands to its initial state once the dose has been administered.

As previously discussed, the resilient member 70 has a substantial degree of flexibility and elasticity in the preferred embodiment of the present invention, primarily for reasons of simplicity and cost. However, it should be expressly understood that other embodiments could be readily substituted for a resilient member 70. For example, a substantially rigid member or face plate backed by a secondary spring 72 could be substituted in FIGS. 19(a)–19(c). The periphery of the rigid member can be sealed to the piston by means of a flexible skirt or a bellows arrangement to maintain a fluid tight region behind the rigid member.

The above disclosure sets forth a number of embodiments of the present invention. Other arrangements or embodiments, not precisely set forth, could be practiced under the teachings of the present invention and as set forth in the following claims.

We claim:

1. An infusion pump comprising:
    a pump housing having an internal chamber and a port for dispensing liquid from said chamber;
    a piston slidably engaging said internal chamber of said pump housing;
    drive means for moving said piston forward toward said port to dispense a series of doses of liquid;
    a flow restrictor restricting the flow of liquid from said chamber through said port, thereby maintaining pressure within said chamber as liquid is dispensed from said chamber; and
    a member extending across at least a portion of said piston, wherein said member moves rearward from an initial position under pressure as said piston moves forward and liquid is dispensed from said chamber, and then gradually returns to said initial position after forward motion of said piston stops and pressure within said chamber decreases, thereby continuing to dispense a small quantity of liquid from said chamber for a period of time after forward motion of said piston stops.

2. The infusion pump of claim 1 further comprising a spring between said piston and said member urging said member to return to said initial position.

3. The infusion pump of claim 1 wherein said member comprises a resilient diaphragm.

4. The infusion pump of claim 3 wherein said resilient diaphragm has a substantially convex cross-sectional shape that collapses under pressure.

5. The infusion pump of claim 3 wherein said resilient diaphragm is attached around the periphery of said piston to define an enclosed region between said resilient diaphragm and said piston.

6. An infusion pump comprising:
    a pump housing having an internal chamber and a port for dispensing liquid from said chamber;
    a piston slidably engaging said internal chamber of said pump housing;
    drive means for moving said piston forward toward said port to dispense a series of doses of liquid;
    a flow restrictor restricting the flow of liquid from said chamber through said port, thereby maintaining pressure within said chamber as liquid is dispensed from said chamber; and
    a resilient member extending across at least a portion of said piston, wherein said resilient member collapses rearward from an initial position under pressure as said piston moves forward and liquid is dispensed from said chamber, and then gradually returns to said initial position after forward motion of said piston stops and pressure within said chamber decreases, thereby continuing to dispense a small quantity of liquid from said chamber for a period of time after forward motion of said piston stops.

7. The infusion pump of claim 6 further comprising a spring between said piston and said resilient member urging said resilient member to return to said initial position.

8. The infusion pump of claim 6 wherein said resilient member comprises a flexible diaphragm.

9. The infusion pump of claim 6 wherein said resilient member has a substantially convex cross-sectional shape.

10. The infusion pump of claim 6 wherein said resilient member is attached around the periphery of said piston to define an enclosed region between said resilient member and said piston.

11. An infusion pump comprising:
    a pump housing having an internal chamber and a port for dispensing liquid from said chamber;
    a piston slidably engaging said internal chamber of said pump housing and having a forward face;
    drive means for moving said piston forward toward said port to dispense a series of doses of liquid;
    a flow restrictor restricting the flow of liquid from said chamber through said port, thereby maintaining pressure within said chamber as liquid is dispensed from said chamber; and
    a substantially convex resilient member attached to the face of said piston forming an enclosed region between said resilient member and said piston, wherein said resilient member moves rearward from an initial position and compresses said enclosed region in response to pressure as said piston moves forward and liquid is dispensed from said chamber, and then gradually returns to said initial position after forward motion of said piston stops and pressure within said chamber decreases, thereby continuing to dispense a small quantity of liquid from said chamber for a period of time after forward motion of said piston stops.

12. The infusion pump of claim 11 further comprising a spring between said piston and said resilient member urging said resilient member to return to said initial position.

13. The infusion pump of claim 11 wherein said resilient member is attached around the periphery of said piston.

14. An infusion pump comprising:
    a pump housing having an internal chamber extending along a longitudinal axis from a proximal opening to a distal port for dispensing liquid from said chamber;
    a flow restrictor restricting the flow of liquid from said chamber and thereby maintaining pressure within said chamber as liquid is dispensed;
    a piston slidably engaging said internal chamber of said pump housing and having:
        (a) a peripheral surface with a sequence of raised steps in a radial pattern spaced at intervals along said axis; and
        (b) a forward face;
    a cap rotatably mounted over said proximal opening of said pump housing, said cap having:
        (a) an arm extending axially forward between said pump housing and said peripheral surface of said piston; and
        (b) a stop extending radially inward from said arm for engaging a selected one of said raised steps at each of a plurality of rotational positions of said cap, thereby selectively limiting axial movement of said piston within said chamber toward said distal port to dispense a predetermined quantity of said liquid;
    a spring between said cap and said piston urging said piston along said axis toward said distal port; and
    a resilient member extending across at least a portion of said face of said piston, wherein said resilient member collapses rearward from an initial position under pressure as said piston moves forward and liquid is dispensed from said chamber, and then gradually returns to said initial position after forward motion of said piston stops and pressure within said chamber decreases, thereby continuing to dispense a small quantity of liquid from said chamber for a period of time after forward motion of said piston stops.

15. The infusion pump of claim 14 further comprising a secondary spring between said piston and said resilient member urging said resilient member to return to said initial position.

16. The infusion pump of claim 14 wherein said resilient member comprises a flexible diaphragm.

17. The infusion pump of claim 14 wherein said resilient member has a substantially convex cross-sectional shape.

18. The infusion pump of claim 14 wherein said resilient member is attached around the periphery of said piston to define an enclosed region between said resilient member and said piston.

* * * * *